US00PP34366P3

(12) United States Plant Patent
Hoekstra

(10) Patent No.: US PP34,366 P3
(45) Date of Patent: Jun. 21, 2022

(54) ***SANSEVIERIA* PLANT NAMED 'OSV SANS 015'**

(50) Latin Name: ***Sansevieria* sp.**
Varietal Denomination: OSV Sans 015

(71) Applicant: ForemostCo., Inc., Miami, FL (US)

(72) Inventor: Folkert Hoekstra, Santa Ana (CR)

(73) Assignee: ForemostCo., Inc., Miami, FL (US)

( * ) Notice: Subject to any disclaimer, the term of this patent is extended or adjusted under 35 U.S.C. 154(b) by 0 days.

(21) Appl. No.: 17/495,906

(22) Filed: Oct. 7, 2021

(65) Prior Publication Data

US 2022/0117139 P1 Apr. 14, 2022

Related U.S. Application Data

(60) Provisional application No. 63/204,558, filed on Oct. 8, 2020.

(51) Int. Cl.
*A01H 5/12* (2018.01)
*A01H 6/32* (2018.01)

(52) U.S. Cl.
USPC ..... Plt./382
CPC ..... *A01H 6/32* (2018.05)

(58) Field of Classification Search
USPC ..... Plt./382, 383
See application file for complete search history.

(56) References Cited

PUBLICATIONS

Tropicos.org. Missouri Botanical Garden. <https://tropicos.org> Retrieved from the Internet Nov. 29, 2021.*

* cited by examiner

*Primary Examiner* — Susan McCormick Ewoldt
(74) *Attorney, Agent, or Firm* — The Webb Law Firm

(57) ABSTRACT

A new and distinct *Sansevieria* plant having deep grey leaves with stacked, dark green horizontal lines and light greenish yellow to white margins.

1 Drawing Sheet

Botanical classification: *Sansevieria* sp.
Varietal denomination: 'OSV Sans 015'.

BACKGROUND OF THE INVENTION

The present invention comprises a new and distinct variety of *Sansevieria* plant, having the varietal name of 'OSV Sans 015' and commercially referred to as "Misty Star". The new variety was discovered and selected by the breeder in a cultivated production bed environment in Williamsburg, Costa Rica as a naturally occurring mutation amongst a population of unpatented and unnamed *Sansevieria* plants. As such, the exact parentage is unknown. The new variety was selected and first asexually reproduced by rhizome cuttings in Williamsburg, Costa Rica. 'OSV Sans 015' has been trial and field tested and has been found to retain its distinctive characteristics and remain true to type through successive propagations. The present invention has not been evaluated under all possible environmental conditions. The phenotype may vary with variations in environment without a change in the genotype of the plant.

When compared to *Sansevieria* variety named 'OSV Sans 013' (U.S. Plant patent application Ser. No. 17/495,894), the new variety exhibits a similar rosette leaf formation with leaves having horizontally stacked lines. However, 'OSV Sans 015' differs from 'OSV Sans 013' in having light greenish yellow to white colored margins and the random presence of faded green, vertical lines. Further, the following characteristics distinguish 'OSV Sans 015' from other *Sansevieria* varieties known to the breeder:

Rosette leaf formation;
Leaves grow upward and then arch outward;
Horizontally stacked and static lines are present across leaves; and
Faded green, vertical lines are randomly present along leaves.

DESCRIPTION OF THE DRAWING

The accompanying photographic drawing taken at approximately 18 weeks of age illustrates the new variety, with the colors being as nearly true as is possible with color illustrations of this type.

DESCRIPTION OF THE PLANT

The following detailed description sets forth the characteristics of the new variety at approximately 2 years of age. The data which defines these characteristics was collected in a greenhouse in September of 2021 in Winter Garden, Fla. Plants of the new variety were grown under 2,000 foot candles of artificial light in 15 cm pots in a climate-controlled greenhouse in Winter Garden, Fla. having 86% relative humidity and an average temperature of 28° C. Color references are primarily to the Munsell Plant Tissue Color Book, 2019 publication, except where general color terms are used.

PLANT

Time to initiate roots: About 12 days at an average of 23° C. night temperatures and 30° C. day temperatures.

Time to develop roots: About 21 days at an average of 23° C. night temperatures and 30° C. day temperatures.
Time to produce a finished plant from a rooted cutting: About 8 weeks in a 15 cm container.
Rooting habit and description: Hair-like roots spread out and wrap at the base.
Form: Spreading.
Height from media surface to top of foliage: 14.0 cm.
Plant diameter: 29.2 cm.
Plant shape: Rosette, having a circular arrangement of the leaves.
Vigor: Strong.
Strength: Rigid, with no need for artificial support.
Disease resistance/susceptibility: Nothing specific noted to date.
Pest resistance/susceptibility: Resistant to thrips and aphids.
Temperature tolerance: Sensitive to temperatures below 7° C. or above 38° C.
Drought tolerance: Very tolerant due to the ability of the leaves to retain water.
Flowers: None observed to date.
Seeds/fruit: None present.
Stem:
*Length.*—1.3 cm.
*Diameter.*—2.0 cm.
*Shape.*—Vertical column
*Color.*—2.5GY 8/2.
*Texture.*—Coriaceous and glabrous.
*Strength.*—Sturdy and rigid.
*Internode length.*—Not applicable.
Leaves:
*Arrangement.*—Basal rosette.
*Average number per plant.*—17.
*Length.*—17.1 cm.
*Width.*—7.0 cm.
*Shape of leaf* (*generally*).—Gladiate.
*Shape of apex.*—Apiculate.
*Shape of base.*—Cuneate.
*Margin description.*—Entire.
*Aspect.*—Mostly erect, arching outwardly to about 50°.
*Texture and luster.*—Upper surface: Coriaceous and glabrous. Lower surface: Coriaceous and glabrous.
*Pubescence.*—Upper surface: None present. Lower surface: None present.
*Fragrance.*—None present.
*Color.*—Young leaves: Upper surface: 5Y 8/4 and 5Y 8/2 margins; 7.5GY 3/4 and 7.5GY 4/4 stacked horizontal lines present on a background of 5GY 4/6. Lower surface: 5GY 4/6 stacked horizontal lines present on a background of 7.5GY 5/6 that fades downward into 7.5GY 7/2; faded 2.5G 7/2 vertical lines present. Mature leaves: Upper surface: 5Y 8/4 and 5Y 8/2 margins; 7.5GY 3/2, 5GY 4/6, and 5GY 6/6 stacked horizontal lines present on a background of 7.5GY 6/6. Lower surface: 5Y 8/4 and 5Y 8/2 margins; 7.5GY 3/4 and 7.5GY 4/6 stacked horizontal lines present on a background of 7.5GY 6/6 that fades downward into 2.5GY 8/2.
*Veins.*—Venation pattern: Parallel. Color: Upper surface: 5GY 4/6 with 7.5GY 3/4 and 7.5GY 4/4 crossing through veins. Lower surface: 7.5GY 6/6 fading downward into 7.5GY 7/2; 5GY 4/6 crossing through veins.
Sheath:
*Length.*—1.5.
*Width.*—3.2.
*Color.*—2.5Y 8/2.
*Texture.*—Coriaceous and glabrous.

I claim:

1. A new and distinct variety of *Sansevieria* plant named 'OSV Sans 015', as is herein illustrated and described.

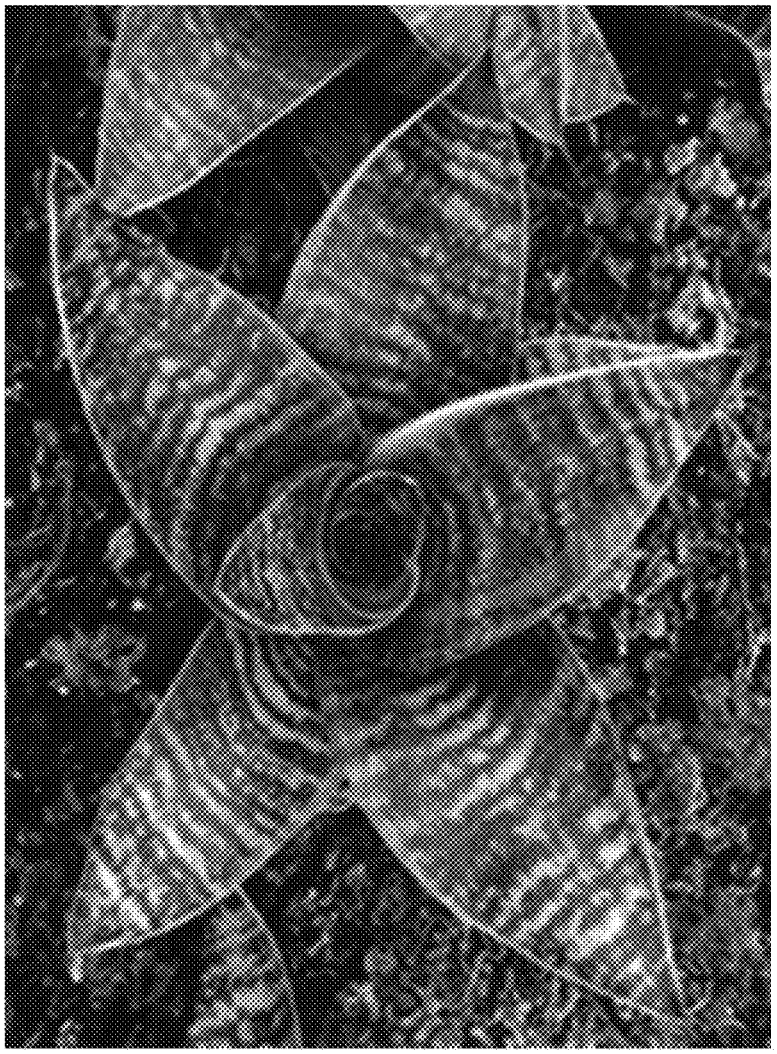

* * * * *